(12) United States Patent
Mohl

(10) Patent No.: US 12,117,007 B1
(45) Date of Patent: Oct. 15, 2024

(54) DEVICE TO ASSIST THE PERFORMANCE OF A HEART

(71) Applicant: Miracor Medical SA, Awans (BE)

(72) Inventor: Werner Mohl, Altenmarkt-Thenneberg (AT)

(73) Assignee: Miracor Medical SA (BE)

( * ) Notice: Subject to any disclaimer, the term of this patent is extended or adjusted under 35 U.S.C. 154(b) by 0 days.

(21) Appl. No.: 18/740,119

(22) Filed: Jun. 11, 2024

Related U.S. Application Data

(60) Continuation of application No. 18/363,166, filed on Aug. 1, 2023, which is a continuation of application
(Continued)

(30) Foreign Application Priority Data

Feb. 27, 2007 (AT) .................. A306/2007

(51) Int. Cl.
| | | |
|---|---|---|
| *A61M 60/148* | (2021.01) | |
| *A61M 60/13* | (2021.01) | |
| *A61M 60/17* | (2021.01) | |
| *A61M 60/237* | (2021.01) | |
| *A61M 60/405* | (2021.01) | |
| *A61M 60/419* | (2021.01) | |

(Continued)

(52) U.S. Cl.
CPC ........... *F04D 13/027* (2013.01); *A61M 60/13* (2021.01); *A61M 60/148* (2021.01); *A61M 60/17* (2021.01); *A61M 60/237* (2021.01); *A61M 60/405* (2021.01); *A61M 60/419* (2021.01); *A61M 60/422* (2021.01); *A61M 60/523* (2021.01); *A61M 60/861* (2021.01); *A61M 60/414* (2021.01); *A61M 60/833* (2021.01)

(58) Field of Classification Search
CPC ................ A61M 60/40; A61M 60/405; A61M 60/148; A61M 60/135; A61M 60/422; A61M 60/857; A61M 60/205; A61M 60/833; A61M 60/414; A61M 1/101; A61M 1/1015; A61M 1/1008; A61M 1/1031; A61M 1/1032; A61M 1/1036; A61M 1/1029; A61M 1/122; A61M 1/125; F04D 13/027
See application file for complete search history.

(56) References Cited

U.S. PATENT DOCUMENTS

| | | |
|---|---|---|
| 3,608,088 A | 9/1971 | Dorman et al. |
| 4,135,253 A | 1/1979 | Reich et al. |

(Continued)

FOREIGN PATENT DOCUMENTS

| | | |
|---|---|---|
| CN | 2412579 Y | 1/2001 |
| DE | 3616857 | 12/1987 |

(Continued)

OTHER PUBLICATIONS

Authorized Officer Malte Kaden, International Search Report for Application No. PCT/IB2008/000421, dated Nov. 7, 2008, 3 pages.

(Continued)

*Primary Examiner* — Tammie K Marlen
(74) *Attorney, Agent, or Firm* — BARNES & THORNBURG LLP; Jeffrey R. Stone

(57) ABSTRACT

A device to assist the performance of a heart with at least one pump that is formed as a rotary pump and driven via a magneto coupling.

25 Claims, 3 Drawing Sheets

Related U.S. Application Data

No. 18/308,958, filed on Apr. 28, 2023, now Pat. No. 11,754,077, which is a continuation of application No. 18/087,083, filed on Dec. 22, 2022, now Pat. No. 11,674,517, which is a continuation of application No. 17/446,046, filed on Aug. 26, 2021, now Pat. No. 11,572,879, which is a continuation of application No. 16/282,948, filed on Feb. 22, 2019, now Pat. No. 11,123,540, which is a continuation of application No. 14/454,965, filed on Aug. 8, 2014, now Pat. No. 10,251,984, which is a continuation of application No. 13/555,318, filed on Jul. 23, 2012, now Pat. No. 8,801,590, which is a division of application No. 12/449,632, filed as application No. PCT/IB2008/000421 on Feb. 27, 2008, now Pat. No. 8,255,050.

(51) Int. Cl.
*A61M 60/422* (2021.01)
*A61M 60/523* (2021.01)
*A61M 60/861* (2021.01)
*F04D 13/02* (2006.01)
*A61M 60/414* (2021.01)
*A61M 60/833* (2021.01)

(56) References Cited

U.S. PATENT DOCUMENTS

| | | |
|---|---|---|
| 4,674,518 A | 6/1987 | Salo |
| 4,895,557 A | 1/1990 | Moise et al. |
| 5,308,319 A | 5/1994 | Ide et al. |
| 5,449,342 A | 9/1995 | Hirose et al. |
| 5,470,208 A | 11/1995 | Kletschka |
| 5,503,615 A | 4/1996 | Goldstein |
| 5,601,418 A | 2/1997 | Ohara et al. |
| 5,676,526 A | 10/1997 | Kuwana et al. |
| 5,695,471 A | 12/1997 | Wampler |
| 5,840,070 A | 11/1998 | Wampler |
| 5,921,913 A | 7/1999 | Siess |
| 5,928,131 A | 7/1999 | Prem |
| 5,947,703 A | 9/1999 | Nojiri et al. |
| 5,964,694 A | 10/1999 | Sicss et al. |
| 6,007,478 A | 12/1999 | Siess et al. |
| 6,053,705 A | 4/2000 | Schob et al. |
| 6,083,260 A | 7/2000 | Aboul-Hosn |
| 6,100,618 A | 8/2000 | Schoeb et al. |
| 6,152,704 A | 11/2000 | Aboul-Hosn et al. |
| 6,155,969 A | 12/2000 | Schima et al. |
| 6,176,848 B1 | 1/2001 | Rau et al. |
| 6,351,048 B1 | 2/2002 | Schob et al. |
| 6,506,146 B1 | 1/2003 | Mohl |
| 6,508,787 B2 | 1/2003 | Erbel et al. |
| 6,540,658 B1 | 4/2003 | Faschiano |
| 6,589,030 B2 | 7/2003 | Ozaki |
| 6,623,475 B1 | 9/2003 | Siess |
| 6,884,210 B2 | 4/2005 | Nose et al. |
| 6,949,066 B2 | 9/2005 | Bearnson et al. |
| 7,699,586 B2 | 4/2010 | LaRose et al. |
| 8,255,050 B2 | 8/2012 | Mohl |
| 8,512,012 B2 | 8/2013 | Akdis et al. |
| 9,616,157 B2 | 4/2017 | Akdis |
| 2001/0039369 A1* | 11/2001 | Terentiev ............ F04D 13/027 600/16 |
| 2004/0236420 A1 | 11/2004 | Yamane et al. |
| 2004/0346420 | 11/2004 | Yamane et al. |
| 2006/0089521 A1 | 4/2006 | Chang |
| 2008/0214888 A1 | 9/2008 | Ben Shalom |
| 2011/0238172 A1* | 9/2011 | Akdis ................ A61M 60/237 623/3.11 |

FOREIGN PATENT DOCUMENTS

| | | |
|---|---|---|
| DE | 19613564 C1 | 1/1998 |
| EP | 0075606 | 4/1983 |
| EP | 0371985 B1 | 6/1990 |
| EP | 0503839 | 9/1992 |
| EP | 1011753 | 6/2000 |
| EP | 1034808 | 9/2000 |
| EP | 0834326 B1 | 11/2004 |
| EP | 1727987 | 12/2006 |
| FR | 1187249 | 8/1959 |
| GB | 2347085 | 8/2000 |
| JP | 2005348996 | 12/2005 |
| WO | WO 1993/20860 | 10/1993 |
| WO | WO 1997/37698 | 10/1997 |
| WO | WO 1999/15213 | 4/1999 |
| WO | WO 2000/44417 | 8/2000 |
| WO | WO 2001/70300 | 9/2001 |
| WO | 2004/098677 A1 | 11/2004 |

OTHER PUBLICATIONS

Merkel et al., "Magnetic Bearing in INCOR Axial Blood Pump Acts as Multifunctional Sensor," Ninth International Symposium on Magnetic Bearings. 2004, 3 pages.

Mohl et al., "Intermittent Pressure Elevation of the Coronary Venous System as a Method to Protect Ischemic Myocardium," Interactive Cardio Vascular and Thoracic Surgery, vol. 4, 2005, pp. 66-69.

Ramsden et al., "A Rotary Blood Pump," University of Technology, Sydney, Mar. 2007, 4 pages.

Syeda et al., "The Salvage Potential of Coronary Sinus Interventions: Meta-Analysis and Pathophysiologic Consequences," The Journal of Thoracic and Cardiovascular Surgery, vol. 127, No. 6 (Jun. 2004), pp. 1703-1712.

Barletta et al., "Design of a Bearingless Blood Pump", Third International Symposium on Magnetic Suspension Technology, pp. 265-274, vol. 1, Jul. 1, 1996.

Bearnson et al., "HeartQuest Ventricular Assist Device Magnetically Levitated Centrifugal Blood Pump", pp. 339-346, published 2006.

Burgreen et al., "Computational Fluid Dynamics Analysis of a Maglev Centrifugal Left Ventricular Assist Device", pp. 874-880, published 2004.

Frazier et al., "Total Heart Replacement with Dual Centrifugal Ventricular Assist Devices", pp. 224-229, ASAIO Journal 2005.

Masuzawa et al., "Magnetically Suspended Centrifugal Blood Pump with an Axially Levitated Motor", pp. 631-638, 2003 International Society for Artificial Organs.

Schob, "Centrifugal pump without bearings or seals", pp. 34-37, World Pumps Jul. 2002.

Qian et al., "Permanent magnetic-levitation of rotating impeller: a decisive breakthrough in the centrifugal pump", pp. 36-38, Journal of Medical Engineering & Technology, vol. 26, No. 1 (Jan./Feb. 2002).

Bourque, et al., "HeartMate III: Pump Design for a Centrifugal LVAD with a Magnetically Levitated Rotor", ASAIO Journal 2001, pp. 401-405.

Bourque, et al., "In Vivo-Assessment of a rotary Left Ventricular Assist Device-induced Artificial Pulse in the Proximal and Distal Aorta", Artif Organs, vol. 30, No. 8, 2006, 6 pgs.

* cited by examiner

DEVICE TO ASSIST THE PERFORMANCE OF A HEART

CROSS-REFERENCE TO RELATED APPLICATIONS

This application is a continuation of U.S. application Ser. No. 18/363,166 filed on Aug. 1, 2023 and is continuation of and claims the benefit of priority to U.S. application Ser. No. 18/308,958 filed on Apr. 28, 2023, which is a continuation of and claims priority to U.S. application Ser. No. 18/087,083 filed on Dec. 22, 2022 (now U.S. Pat. No. 11,674,517), which is a continuation of and claims priority to U.S. application Ser. No. 17/446,046 filed on Aug. 26, 2021 (now U.S. Pat. No. 11,572,879), which is a continuation of U.S. application Ser. No. 16/282,948 filed on Feb. 22, 2019 (now U.S. Pat. No. 11,123,540), which is a continuation of U.S. application Ser. No. 14/454,965 filed on Aug. 8, 2014 (now U.S. Pat. No. 10,251,984), which is a continuation of U.S. application Ser. No. 13/555,318 filed on Jul. 23, 2012 (now U.S. Pat. No. 8,801,590), which is a divisional of U.S. application Ser. No. 12/449,632 filed on Aug. 18, 2009 (now U.S. Pat. No. 8,255,050), which is the U.S. national phase of International Application PCT/IB2008/000421 filed on Feb. 27, 2008, which designated the U.S. and claims benefit of AT A 306/2007 filed Feb. 27, 2007, the entire contents of these prior applications are hereby incorporated by reference.

BACKGROUND

After a heart failure, for example a cardiac infarction or other reasons for the decrease in the performance of a heart, it is of essential importance for intensive care medicine to normalise and stabilise the cardiac function again as rapidly as possible. When for example the volume output of the heart is distinctly reduced as a result of a failure, it is particularly important to reliably and rapidly re-establish a corresponding peripheral blood flow in order to prevent secondary damage. The use of heart-lung machines basically allows the essential vital functions to be maintained. A specific adaptation to the respective actual requirements generally does not take place with such devices, however. Rather, conventional heart-lung machines are devices which, using external pumps, maintain a forced circulation of blood without systematically entering into the respective requirements of the heart which has been weakened or subjected to a failure.

In surgical interventions, particularly in the vein area, it has already been proposed to carry out retroinfusion, controlled by venous pressure, from or in veins of the body with the suction" of fluid and return of the fluid via a pump. Conventional catheters are used here, the lumina of which allow a suction of fluid and via the lumina of which the return is made possible at a suitable site. Known devices, particularly for the retroinfusion of blood in coronary veins in the area of myocardial protection during a brief coronary artery closure within a cardiological intervention, are generally devised so that a balloon dilatation of an arteriosclerotically constricted coronary artery is carried out. In these cases, a compensation which is adapted to the intervention briefly taking place respectively can be carried out by the return of blood which has been drawn off in veins. For a continuous restitution of the full function of a heart, however, the criteria are not taken into account which would be relevant for the full function of the heart, and an intensive provision over a particular period of time is therefore not provided with such devices. At the same time, the provision of the other organs must also be maintained.

In the device known from AT 407 960 B for assisting the performance of a heart, fluid is removed from blood vessels via an external pump and is returned into blood vessels via a return catheter, in which the returned quantity of fluid is regulated as a function of measurement values, with a heart ventricle catheter being provided to obtain these measurement values. The known device comprised a heart ventricle catheter which is equipped in the cardiac chamber with sensors to measure the volume of fluid per unit of time, in which these sensors, in the introduced state of the heart ventricle catheter, lie in the cardiac chamber and these sensors are connected with an evaluation circuit in which the ratio of the diastolic volume to the systolic volume is evaluated per heartbeat or per unit of time in particular the discharge rate and/or the deviation of the volume conveyed per unit of time by the heart from a defined rated value is evaluated, for example the rated value, calculated from physically specific data for the cardiac output. The signal which is generated in this way is passed to the pump, via which fluid is withdrawn from the cardiac chamber and is recirculated as a function of the generated signal.

SUMMARY

A fluid flow which is improved by the pump is to be developed in a way in which the mechanical stress of highly sensitive fluids, such as blood for example, can be kept as low as possible and nevertheless the corresponding improvement to circulation can be ensured at desired locations. A completely impervious separation of the rotor from the drive wheel is achieved by a magneto coupling which is provided according to the invention, which eliminates axial passages between the drive wheel and the rotor lying distally on the outside.

The rotor itself can follow design principles such as described for example in WO 01/70300 A1. The rotary pump shown and described there for conveying blood and other highly sensitive fluids is formed as an external electromagnetically driven pump which is not directly suitable for incorporation into a catheter. However, for the desired conveying capacity with the axial pump according to the invention, provision is also made according to the invention that the rotor has guide surfaces to produce centrifugal flow components.

The driving fluid can be used within the scope of the invention in order to be able to operate a balloon for retroperfusion. The embodiment is preferably devised hereby so that the lumina for the driving fluid are guided through an expandable balloon surrounding the catheter in a sealing manner, and that the lumina have separately controllable closure members via which driving fluid can arrive in the balloon or out of the balloon into the respective lumina, in which preferably the closure members are formed as magneto valves. On inflation of the balloon, additional driving medium is required which can be discharged again on collapsing of the balloon. This is possible extracorporally on the drive side by means of a reservoir.

The embodiment to assist the performance of a heart according to the invention, in which fluid is conveyed in blood vessels with the use of a pump and the conveyed quantity is able to be regulated as a function of measurement values of a heart ventricle catheter, from which the cardiac output is determined, proceeds from a development according to AT 407 960 B and is characterised substantially in that the pump is formed as an intravasal rotary pump at the periphery or at the distal end of the catheter, the rotor of which, lying on the outside, is connected via a magneto coupling with the drive which is arranged inside the catheter.

BRIEF DESCRIPTION OF DRAWINGS

The invention is explained in further detail below by use of an examplary embodiment which is illustrated diagrammatically in the drawings, in which.

DETAILED DESCRIPTION

Figure 1:
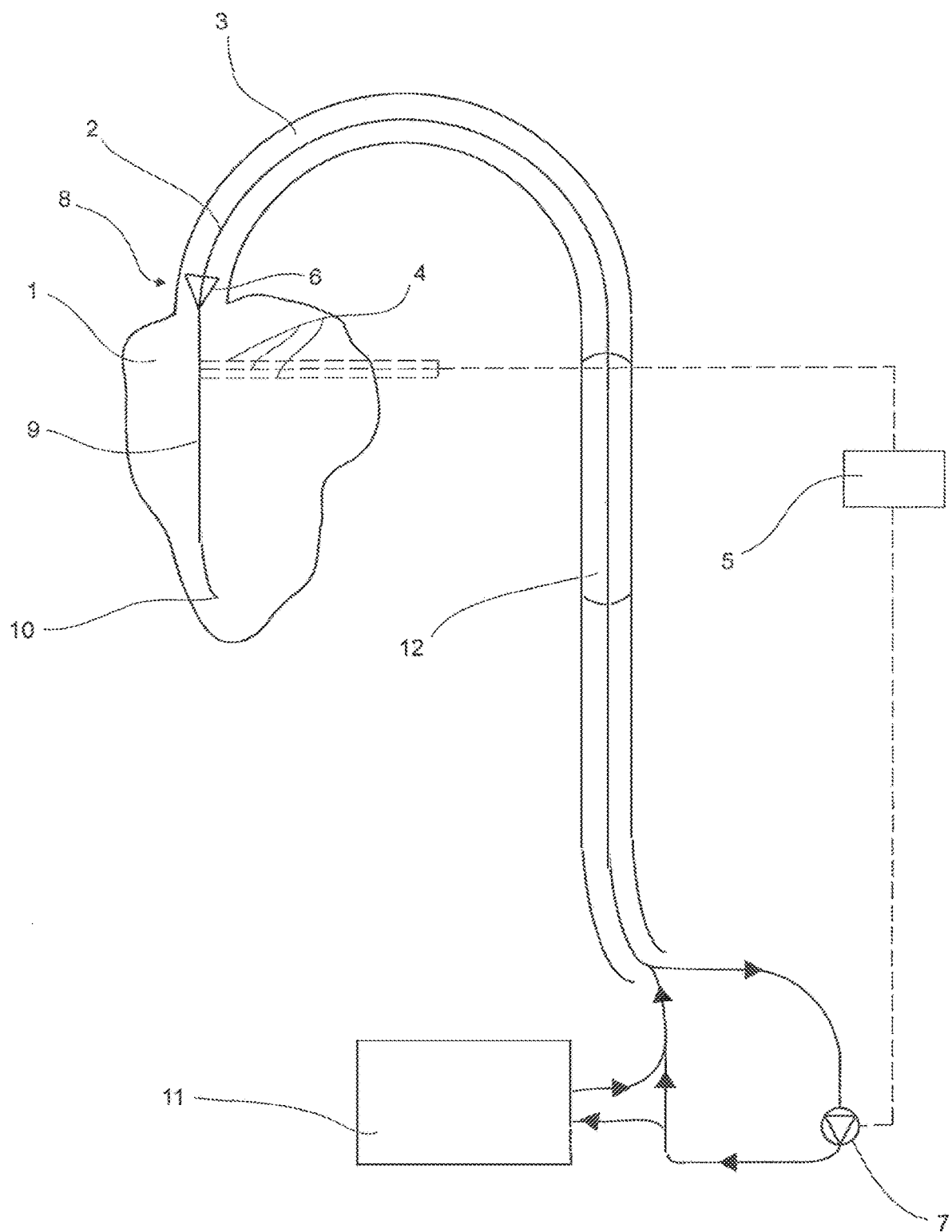
FIG. 1 shows a diagrammatic illustration of the arrangement of the pump and of the drive.

In FIG. 1, a heart is designated by 1, into which a heart ventricle catheter 2 is introduced. The catheter is introduced here for example via the femoral artery and the aortic arch 3 into the heart chamber and carries a series of sensors 4 via which the volume can be determined. The measurement signals are passed to a control arrangement 5. The heart ventricle catheter is formed with several lumina, as additionally illustrated below in further figures of the drawings, with fluid being supplied via such lumina to drive a rotor, arranged at the distal end, which forms the pump to assist the blood circulation and is designated by 6 in FIG. 1. The positioning of this rotor is indicated in FIG. 1 by the arrow 8. The driving medium for the rotor or the pump is guided in a circular flow by means of a fluid pump 7 which can be regulated in a synchronised manner as a function of the control signals generated in the control arrangement 5. The distal region in which the pump is arranged is designated diagrammatically by 8, the catheter 2 having at its distal end a tube 9 leading to the suction end 10. A reservoir for driving fluid is designated by 11, which provides additional driving medium for filling the balloon 12 serving for an occlusion of the artery, and which receives again the volume of driving medium occurring on deflation of the balloon.

The volumetric measurement in the cardiac chamber allows differences to be reliably detected between the diastolic and systolic volume and allows corresponding correction signals to be made available for the output of the synchronised fluid pump 7. Furthermore, in the control circuit 5, corresponding fixed values can be provided, such as for example a defined cardiac output, which is referred to on deviation of the measured cardiac output to control the pump.

A retroperfusion can take place via a conventional balloon catheter which is occluded in a correspondingly synchronized manner, so that the directed return is in fact guaranteed during the diastole. Hereby the corresponding measurement values for the heart rate or for the correct moment of the diastole can be obtained from ECG data.

Figure 2:
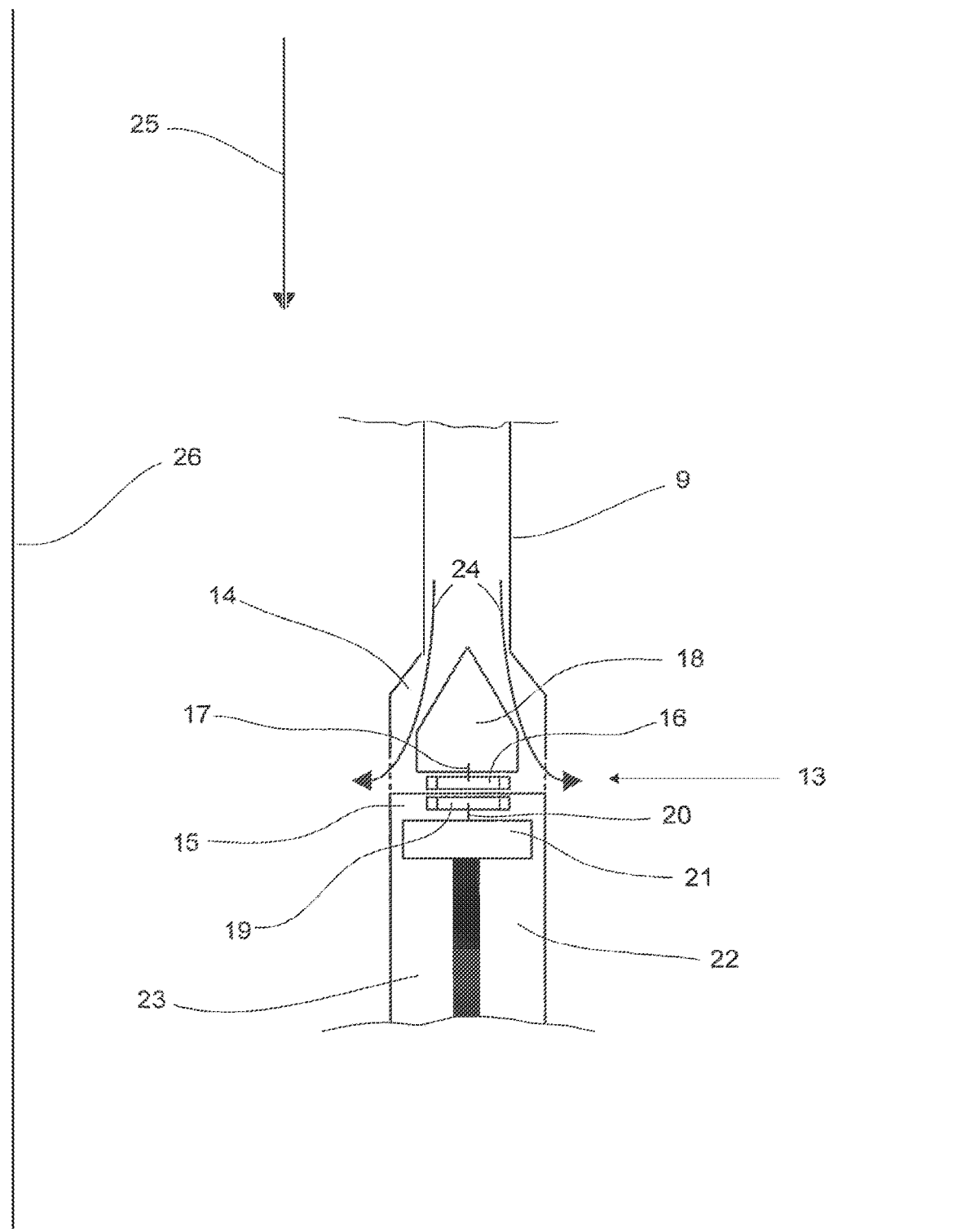
FIG. 2 shows a diagrammatic illustration of the distal end of a catheter which is used according to the invention.

In FIG. 2, the distal end of a modified catheter 2 is now illustrated. The end side 13 of this catheter has two pocket-shaped chambers 14 and 15, in which bar magnets are respectively arranged. The bar magnet 16 is connected here at the distal end outwards via a shaft 17 with a rotor 18, whereas the bar magnet 19 lying on the inside is connected via a shaft 20 with a drive wheel 21. The drive wheel 21 is formed here as a paddle wheel and is acted upon with fluid via a lumen 22, this fluid flowing off again via the lumen 23 of the catheter. The rotation of the paddle wheel 21 is regulated here accordingly by corresponding control of the fluid pressure in the lumen 22 serving for the supply of fluid, in which the magnet 19, which is connected so as to be locked against relative rotation with the paddle wheel 21, is set into corresponding rotation. At the outer side, which is completely sealed with respect to the lumina 22 and 23, the magnet 16 is subsequently entrained accordingly and drives the rotor 18 via the shaft 17, whereby a flow is formed in the region of the tube 9, as is indicated by the arrows 24, and which assists the natural blood flow in the vessel 26, illustrated by the arrow 25.

Figure 3:
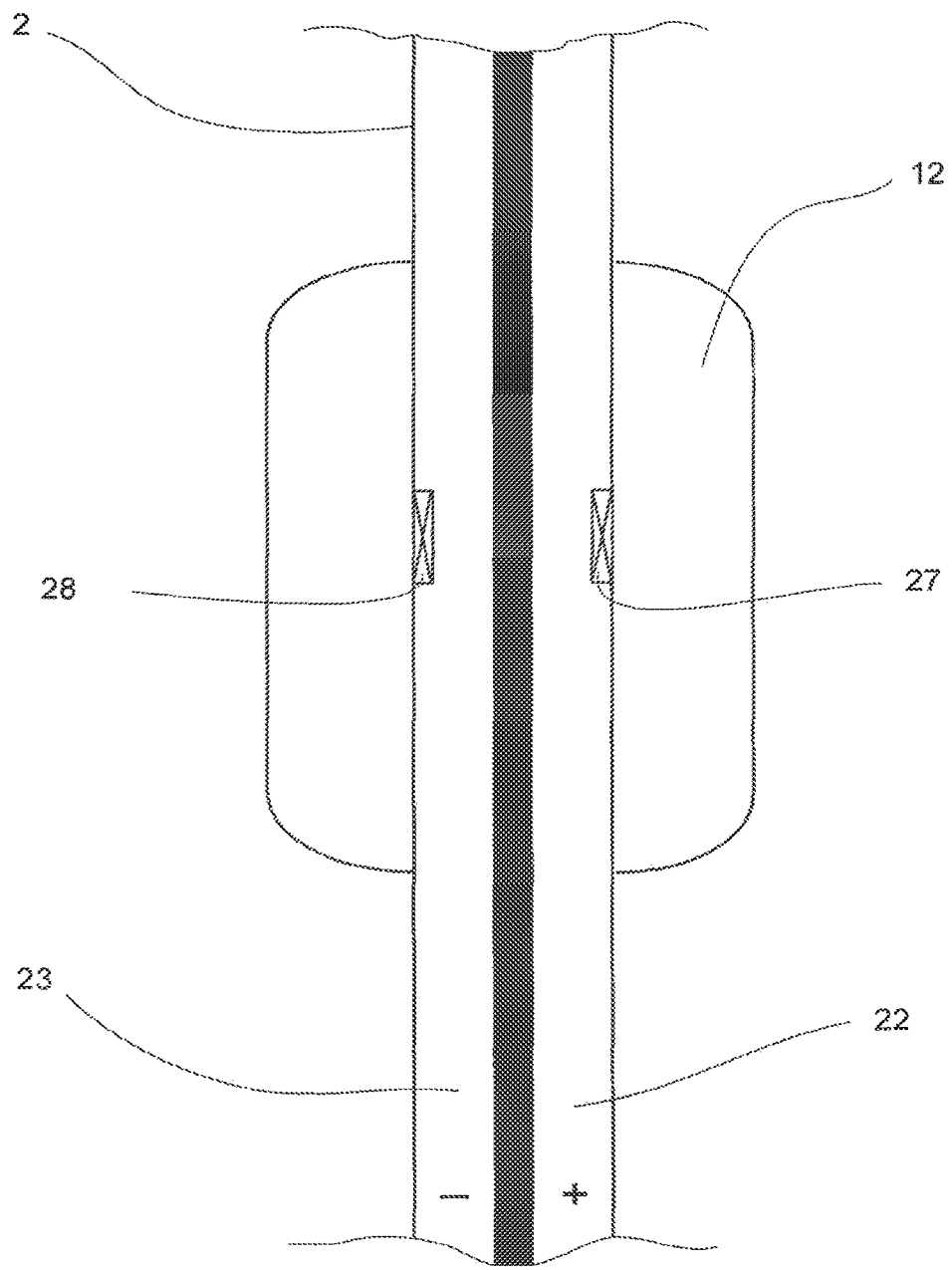
FIG. 3 shows an enlarged illustration of the part of the catheter bearing the balloon, in section.

In FIG. 3, the partial region of the balloon 12, which is connected in a sealing manner to the catheter 2, is illustrated on an enlarged scale. The two lumina leading away from the fluid pump 7 and back to the fluid pump 7 are designated in turn by 22 and 23. In the region of the balloon 12, the wall of these lumina is provided with valves which can be actuated magnetically for example. The valves are indicated diagrammatically by 27 and 28. An opening of the valve 27 leads to the fluid, coming from the fluid pump 7, which is under pressure, which is indicated by the "+" sign, being pumped into the balloon 12, with which the overall quantity of the circulating driving fluid would of course be reduced, in so far as the reservoir 11, indicated diagrammatically in FIG. 1, is not provided. By closing the valve 27, the occlusion is closed off, the collapsing of the balloon 12 being able to be brought about by opening the valve 28 and the fluid now being drawn off via the lumen 23, leading back to the pump, which lumen 23 is at a slightly lower pressure which is indicated by the "−" sign. As the overall volume of the fluid in the circulating system is now to be reduced, a portion of this volume must be pumped back again into the reservoir 11 according to FIG. 1.

The invention claimed is:

1. A heart assist pump device configured to be positioned within a body and comprising:

an inflow tube with a suction end configured to be inserted into a ventricle of a heart, and comprising a central axis, the inflow tube defining a path for blood to flow therethrough;

a magnetically driven rotor, and a first magnetic device associated with the magnetically driven rotor, the magnetically driven rotor and first magnetic device axially aligned with the central axis of the inflow tube, the magnetically driven rotor comprising guide surfaces in fluid communication with the blood flowing in a downstream direction through the inflow tube and configured to produce centrifugal flow components within the blood;

a second magnetic device axially aligned with the central axis of the inflow tube, the second magnetic device configured to rotate the magnetically driven rotor via a magneto coupling and wherein the second magnetic device is axially spaced from the guide surfaces of the magnetically driven rotor;

a first chamber defined by one or more walls and that is aligned with the central axis and in fluid communication with the inflow tube, the first chamber having walls including a sidewall and a bottom wall having an inner surface that is located at a position that is axially opposite of the suction end of the inflow tube, wherein the inner surface of the bottom wall is substantially entirely planar;

wherein the guide surfaces are oriented within the first chamber and wherein the magnetically driven rotor is configured to rotate the guide surfaces about the central axis within the first chamber, wherein a gap is defined between the sidewall of the first chamber and the guide surfaces, the gap configured to provide a blood flow path,
  a second chamber that surrounds the second magnetic device and comprises one or more walls that seal the second magnetic device from the magnetically driven rotor and the first magnetic device, and
  a defined blood outflow path in fluid communication with the first chamber and configured to direct blood driven by the magnetically driven rotor in a direction that not aligned with the inflow tube and the central axis.

2. The heart assist pump device of claim 1, wherein the guide surfaces are spaced axially away from the inner surface of the bottom wall of the first chamber.

3. The heart assist pump device of claim 1, wherein the second magnetic device is axially spaced from the first chamber.

4. The heart assist pump device of claim 3, wherein the second magnetic device is positioned axially adjacent to, and sealed from, the first chamber.

5. The heart assist pump device of claim 1, wherein the direction of the blood driven by the magnetically driven rotor is substantially perpendicular to the inflow tube and the central axis for at least a portion of the defined blood outflow path.

6. The heart assist pump device of claim 1, wherein the first magnetic device and the second magnetic device are positioned such that at least a portion of the first magnetic device and at least a portion of the second magnetic device are in spaced-apart overlapping axial alignment.

7. The heart assist pump device of claim 1, wherein the first magnetic device is rigidly coupled to the magnetically driven rotor.

8. The heart assist pump device of claim 1, wherein the guide surfaces of the rotor are configured to drive the blood within the first chamber in a direction that is substantially perpendicular to the inflow tube and the central axis.

9. The heart assist pump device of claim 1, further comprising a control arrangement configured to control the heart assist pump device comprising at least one sensor configured to generate a control signal and a controller configured to receive the generated control signal.

10. The heart assist pump device of claim 1, wherein the ventricle is a left ventricle.

11. The heart assist pump device of claim 10, wherein the blood vessel is an artery.

12. The heart assist pump device of claim 11, wherein the artery is an aorta.

13. A method for assisting the blood circulation of a heart in a body, comprising:
  providing a heart assist pump device configured to be positioned within the body and comprising:
an inflow tube with a suction end configured to be inserted into a ventricle of the heart, and comprising a central axis, the inflow tube defining a path for blood to flow therethrough;
  a magnetically driven rotor, and a first magnetic device associated with the magnetically driven rotor, the magnetically driven rotor and first magnetic device axially aligned with the central axis of the inflow tube, the magnetically driven rotor comprising guide surfaces in fluid communication with the blood flowing in a downstream direction through the inflow tube and configured to produce centrifugal flow components within the blood;
  a second magnetic device axially aligned with the central axis of the inflow tube, the second magnetic device configured to rotate the magnetically driven rotor via a magneto coupling and wherein the second magnetic device is axially spaced from the guide surfaces of the magnetically driven rotor;
  a first chamber defined by one or more walls and that is aligned with the central axis and in fluid communication with the inflow tube, the first chamber having walls including a sidewall and a bottom wall having an inner surface that is located at a position that is axially opposite of the suction end of the inflow tube, wherein the inner surface of the bottom wall is substantially entirely planar;
  wherein the guide surfaces are oriented within the first chamber and wherein the magnetically driven rotor is configured to rotate the guide surfaces about the central axis within the first chamber,
  wherein a gap is defined between the sidewall of the first chamber and the guide surfaces, the gap configured to provide a blood flow path,
  a second chamber that surrounds the second magnetic device and comprises one or more walls that seal the second magnetic device from the magnetically driven rotor and the first magnetic device, and
  a defined blood outflow path in fluid communication with the first chamber and configured to direct blood driven by the magnetically driven rotor in a direction that is not aligned with the inflow tube and the central axis;
  inserting the suction end of the inflow tube into the ventricle of the heart, activating the heart assist pump device;
  rotating the magnetically driven rotor via the magneto coupling;
  suctioning the blood from the ventricle and into the inflow tube;
driving the blood through the blood outflow port; and
returning the driven blood to a blood vessel of the body.

14. The method of claim 13, wherein the guide surfaces are spaced axially away from the inner surface of the bottom wall of the first chamber.

15. The method of claim 13, wherein the second magnetic device is axially spaced from the first chamber.

16. The method of claim 15, wherein the second magnetic device is positioned axially adjacent to, and sealed from, the first chamber.

17. The method of claim 13, wherein the direction of the blood driven by the magnetically driven rotor is substantially perpendicular to the inflow tube and the central axis for at least a portion of the defined blood outflow path.

18. The method of claim 13, wherein the first magnetic device and the second magnetic device are positioned such that at least a portion of the first magnetic device and at least a portion of the second magnetic device are in spaced-apart overlapping axial alignment.

19. The heart assist pump device of claim 13, wherein the first magnetic device is rigidly coupled to the magnetically driven rotor.

20. The method of claim 13, wherein the guide surfaces of the rotor are configured to drive the blood within the first chamber in a direction that is substantially perpendicular to the inflow tube and the central axis.

21. The method of claim 13, wherein the heart assist pump device comprises a control arrangement configured to control the heart assist pump device comprising at least one sensor configured to generate a control signal and a controller configured to receive the generated control signal.

22. The method of claim 21, further comprising:
  controlling the heart assist pump device based on the generated control signal.

23. The method of claim 13, wherein the ventricle is a left ventricle.

24. The method of claim 23, wherein the blood vessel is an artery.

25. The method of claim 24, wherein the artery is an aorta.

* * * * *